US011154607B2

(12) United States Patent
Shackelton et al.

(10) Patent No.: US 11,154,607 B2
(45) Date of Patent: Oct. 26, 2021

(54) GENETICALLY ATTENUATED NUCLEIC ACID VACCINE

(71) Applicants: Laura Shackelton, Sammamish, WA (US); Matthew Kerner, Sammamish, WA (US)

(72) Inventors: Laura Shackelton, Sammamish, WA (US); Matthew Kerner, Sammamish, WA (US)

( * ) Notice: Subject to any disclaimer, the term of this patent is extended or adjusted under 35 U.S.C. 154(b) by 45 days.

(21) Appl. No.: 16/616,402

(22) PCT Filed: Jun. 1, 2018

(86) PCT No.: PCT/US2018/035591
§ 371 (c)(1),
(2) Date: Nov. 22, 2019

(87) PCT Pub. No.: WO2018/222986
PCT Pub. Date: Dec. 6, 2018

(65) Prior Publication Data
US 2020/0138937 A1    May 7, 2020

Related U.S. Application Data

(60) Provisional application No. 62/514,096, filed on Jun. 2, 2017.

(51) Int. Cl.
*A61K 39/12* (2006.01)
*A61K 9/00* (2006.01)
*A61K 39/00* (2006.01)

(52) U.S. Cl.
CPC ............ *A61K 39/12* (2013.01); *A61K 9/0019* (2013.01); *A61K 2039/51* (2013.01); *A61K 2039/6018* (2013.01)

(58) Field of Classification Search
None
See application file for complete search history.

(56) References Cited

U.S. PATENT DOCUMENTS

| 4,687,737 A | 8/1987 | Sharp et al. |
| 9,121,024 B2 | 9/2015 | Tian et al. |

(Continued)

FOREIGN PATENT DOCUMENTS

WO    WO 2010/037062 A1    4/2010

OTHER PUBLICATIONS

ISR and Written Opinion dated Sep. 7, 2018 in PCT/US2018/035591, 45 pages.

(Continued)

*Primary Examiner* — Michelle S Horning
(74) *Attorney, Agent, or Firm* — Leydig, Voit & Mayer, Ltd.

(57) ABSTRACT

The disclosed compositions and methods provide an approach for the rational development of a nucleic acid vaccine. Methods are disclosed to deliver a viral genome, and/or a representative or derivative of such, that is attenuated but can, when co-delivered with unreplicable compensatory translational tools to a host cell, initially generate phenotypically wild-type, genetically attenuated viruses which infect subsequent cells and elicit a relevant and robust immune response. However, progeny of this initial generation, lacking the compensatory tools delivered to the initial host cells, are both phenotypically and genetically attenuated, thereby compromised in their ability to induce disease.

16 Claims, 4 Drawing Sheets

Specification includes a Sequence Listing.

(56) References Cited

U.S. PATENT DOCUMENTS

2013/0323821 A1\* 12/2013 Tian ............... C12N 15/70
  435/252.33
2016/0317647 A1\* 11/2016 Ciaramella .......... A61K 9/0019

OTHER PUBLICATIONS

Mühlhausen et al. (publicly available May 2016) "A novel nuclear genetic code alteration in yeasts and the evolution of codon reassignment in eukaryotes" *Genome Res.* May 2016, 26(7): 945-955.
National Center for Biotechnology Information "NCBI", ("Genetic Codes", 2017 (online): pdf p. 1).
Ohama et al. (1993) "Non-Universal Decoding of the Leucine Codon CUG in Several *Candida* Species." *Nucleic Acids Research* 21(17): 4039-4045.
Stanton (Apr. 2017) "CHO stopper? Biogen looks to alternative cell lines for future of bioproduction" *BioPharma Reporter*, available online at https://www.biopharma-reporter.com/Article/2017/04/28/Biogen-working-on-a-radical-departure-from-the-CHO-platform, 2 pages.
Timmer (Dec. 2016) "Virus engineered to rely on artificial amino acids, used as vaccine" *ARS Technica*, available online at https://arstechnica.com/science/2016/12/virus-engineered-to-rely-on-artificial-amino-acids-used-as-vaccine/, 5 pages.
Wang et al. (2014) "Construction of a live-attenuated HIV-1 vaccine through genetic code expansion" Angew Chem Int Ed Engl. 53(19): 4867-4871.

\* cited by examiner

Attenuated Virus

5' ... CUG ... CUG ... 3'

Leu
Leu

Weakened/poor/inefficient subsequent rounds of infection in host

5' ... CUG ... CUG ... 3'

Leu

Host Cell

Fig. 4

SEQUENCE LISTING

```
<160> NUMBER OF SEQ ID NOS: 6

<210> SEQ ID NO 1
<211> LENGTH: 21
<212> TYPE: RNA
<213> ORGANISM: Artificial Sequence
<220> FEATURE:
<223> OTHER INFORMATION: synthetic

<400> SEQUENCE: 1
augauaacau cuaaaagauc c                                                21

<210> SEQ ID NO 2
<211> LENGTH: 7
<212> TYPE: PRT
<213> ORGANISM: Artificial Sequence
<220> FEATURE:
<223> OTHER INFORMATION: synthetic

<400> SEQUENCE: 2

Met Ile Thr Ser Lys Arg Ser
1               5

<210> SEQ ID NO 3
<211> LENGTH: 21
<212> TYPE: RNA
<213> ORGANISM: Artificial Sequence
<220> FEATURE:
<223> OTHER INFORMATION: synthetic

<400> SEQUENCE: 3
augauaacac ugaaaagacu g                                                21

<210> SEQ ID NO 4
<211> LENGTH: 7
<212> TYPE: PRT
<213> ORGANISM: Artificial Sequence
<220> FEATURE:
<223> OTHER INFORMATION: synthetic
```

```
<400> SEQUENCE: 4

Met Ile Thr Leu Lys Arg Leu
1               5

<210> SEQ ID NO 5
<211> LENGTH: 7
<212> TYPE: PRT
<213> ORGANISM: Artificial Sequence
<220> FEATURE:
<223> OTHER INFORMATION: synthetic

<400> SEQUENCE: 5

Met Ile Thr Ser Lys Arg Leu
1               5

<210> SEQ ID NO 6
<211> LENGTH: 7
<212> TYPE: PRT
<213> ORGANISM: Artificial Sequence
<220> FEATURE:
<223> OTHER INFORMATION: synthetic

<400> SEQUENCE: 6

Met Ile Thr Leu Lys Arg Ser
1               5
```

GENETICALLY ATTENUATED NUCLEIC ACID VACCINE

CROSS-REFERENCE TO RELATED APPLICATIONS

This application is a U.S. National Stage Application filed under 35 U.S.C. § 371 of International Application No. PCT/US2018/035591, filed Jun. 1, 2018, which claims the priority benefit of U.S. Provisional Application No. 62/514,096, filed Jun. 2, 2017. Both of these applications are hereby incorporated by reference in their entireties.

REFERENCE TO A SEQUENCE LISTING

The Sequence Listing written in file "Sequence Listing ST25", created on Jun. 27, 2018, 1,303 bytes, containing SEQ ID Nos 1-6 is provided herewith in a computer-readable nucleotide/amino acid .txt file and is specifically incorporated by reference.

FIELD OF THE INVENTION

The present invention relates to compositions and methods of producing genetically attenuated nucleic acid vaccines.

BACKGROUND OF THE INVENTION

Live attenuated viral vaccines are some of the most effective vaccines currently used. Unlike inactivated or recombinant subunit vaccines, live attenuated viral vaccines infect the cells and replicate (to some extent), more closely mimicking a natural infection and, thus, inducing a more relevant immune response (e.g., presentation of intracellular foreign peptides on MHC class I molecules). Live attenuated vaccines include human measles, mumps, rubella, OPV, VZV, smallpox, yellow fever, and rotavirus vaccines, as well as several veterinary vaccines. To generate live attenuated vaccines, wild-type viruses have often been attenuated via passage in an unnatural host/tissue culture, in which they accumulate random mutations, some of which result in attenuation in the natural host but still allow for sufficient replication/propagation in cell culture. It is an inefficient empirical approach that relies on chance mutations.

Alternative, more rational approaches that have been attempted include introducing suboptimal codons for a given amino acid, reducing the efficiency of viral production; and cell line complementation, where, e.g., critical viral genes are removed from the virus and introduced into the production cell line, enabling the generation of structurally wild-type viral particles that encapsulate an incomplete genome. Such an approach generates a replication-incompetent vaccine where the viral vaccine can initially infect the vaccinee's cells, but, as the vaccinee's cells do not include the missing viral genes, they cannot generate live viruses and further propagate the infection.

Ideally, a live attenuated vaccine maintains the ability to infect cells and replicate/spread to a sufficient extent to induce a robust immune response, but without inducing disease. In sum, the challenge is generating a virus that replicates reliably and to a very high titer in the manufacturing cell lines, hence reducing production costs, yet is attenuated in the vaccinee—i.e., is weakened to the point where it replicates in the vaccinee and maintains most, if not all, of the relevant epitopes as the wild-type virus, to generate robust immunity, but is not virulent enough to cause disease.

SUMMARY OF THE INVENTION

The compositions and methods described herein provide live, genetically attenuated nucleic acid-based viral vaccines. An attenuated viral nucleic acid, representing the complete viral genome (in a replicable and translatable form) with select mutations, is introduced into the cell of a vaccinee together with unreplicable compensatory translational tools, which compensate for the select mutations, and which together have the capacity to generate a phenotypically wild-type, genetically attenuated virus in the initial cell of the vaccinee. The resultant virus generates a relevant and robust immune response and infects a subsequent cell as a wild type virus would, but any progeny of this virus, lacking the compensatory translational tools in the subsequently infected vaccinee cells, are phenotypically and genetically attenuated and unable to induce disease.

In one aspect, a RNA whole genome viral vaccine is attenuated via the substitution of codons for a first amino acid with the codons for a second, different amino acid and complemented with synthetic tRNAs with anticodons corresponding to the introduced codon coding for the second amino acid but charged with the first amino acid. When the genome and/or the positive sense of such is co-delivered with such artificially charged tRNA into a host cell, the viral vaccine results in a phenotypically wild-type, genetically attenuated virus. During further propagation in the host, the viral vaccine results in a phenotypically and genetically attenuated virus.

In one aspect, a DNA whole genome viral vaccine is attenuated via the substitution of codons for a first amino acid with the codons for a second, different amino acid and complemented with synthetic tRNAs with anticodons corresponding to the introduced codon coding for the second amino acid but charged with the first amino acid. When the genome and/or the mRNA of such is co-delivered with such artificially charged tRNA into a host cell, the viral vaccine results in a phenotypically wild-type, genetically attenuated virus. During further propagation of the virus in the host, the viral vaccine results in a phenotypically and genetically attenuated virus.

In another aspect, the method of making a nucleic acid vaccine comprises substituting one or more codons for a first amino acid encoded by a viral nucleic acid with a codon for a second, different amino acid resulting in a modified viral nucleic acid; artificially charging one or more tRNAs, having an anticodon corresponding to the introduced codon coding for the second amino acid, yet charged with the first amino acid; and packaging the modified viral nucleic acid and artificially charged tRNA in a delivery system for co-delivery to a vaccinee.

In a further aspect, a nucleic acid vaccine is produced by a method comprising: substituting one or more codons for a first amino acid encoded by a viral nucleic acid with a codon for a second, different amino acid resulting in a modified viral nucleic acid; artificially charging one or more tRNAs, having an anticodon corresponding to the introduced codon coding for the second amino acid, with the first amino acid; and packaging the modified viral nucleic acid and artificially charged tRNA in a delivery system for co-delivery to a vaccinee.

The viral nucleic acid of the compositions and methods disclosed herein can be positive sense RNA and/or mRNA derived from and representing, and in some instances in addition to, the corresponding positive sense RNA, DNA, negative sense RNA, or double-stranded RNA and combinations thereof. The viral nucleic acid can be a whole viral genome or a portion of a viral genome.

References to viral genome or genome can be understood to be the genome itself, the positive sense of such, and/or the derived mRNA. The latter two would be the primary candidates for co-delivery with the tRNA in the vaccine to allow for direct translation.

The delivery system for the compositions and methods disclosed herein is selected from lipid nanoparticle, cationic emulsion (CNE), medium for electroporation, novel delivery methods, and combinations thereof. The lipid nanoparticle can be a liposome.

In another aspect, a method of increasing immunity in a host to a virus is disclosed, comprising administering to the host a nucleic acid vaccine as disclosed herein.

In another aspect, the subject of the vaccination is a human, livestock, a bird, a household pet, wildlife, or a plant.

In another aspect, the virus from which the nucleic acid vaccine is derived is selected from the group consisting of Influenza virus, respiratory syncytial virus (RSV), poliovirus, Hepatitis C virus, West Nile virus, Zika virus, Chikungunya virus, Ebola virus, Lassa virus, Dengue virus, SARS coronavirus, Middle East Respiratory Syndrome (MERS) coronavirus, Cytomegalovirus, Herpes Simplex viruses, Rabies virus, Foot and Mouth Disease Virus, Noroviruses, Enteroviruses, newly emerging viruses, as well as combinations thereof.

BRIEF DESCRIPTION OF THE DRAWINGS

FIG. 2 also shows translation of the RNA vaccine with the compensatory artificial and mismatched tRNA resulting in initial generation of the phenotypically wild-type, genetically attenuated virus.

Figure 1A:
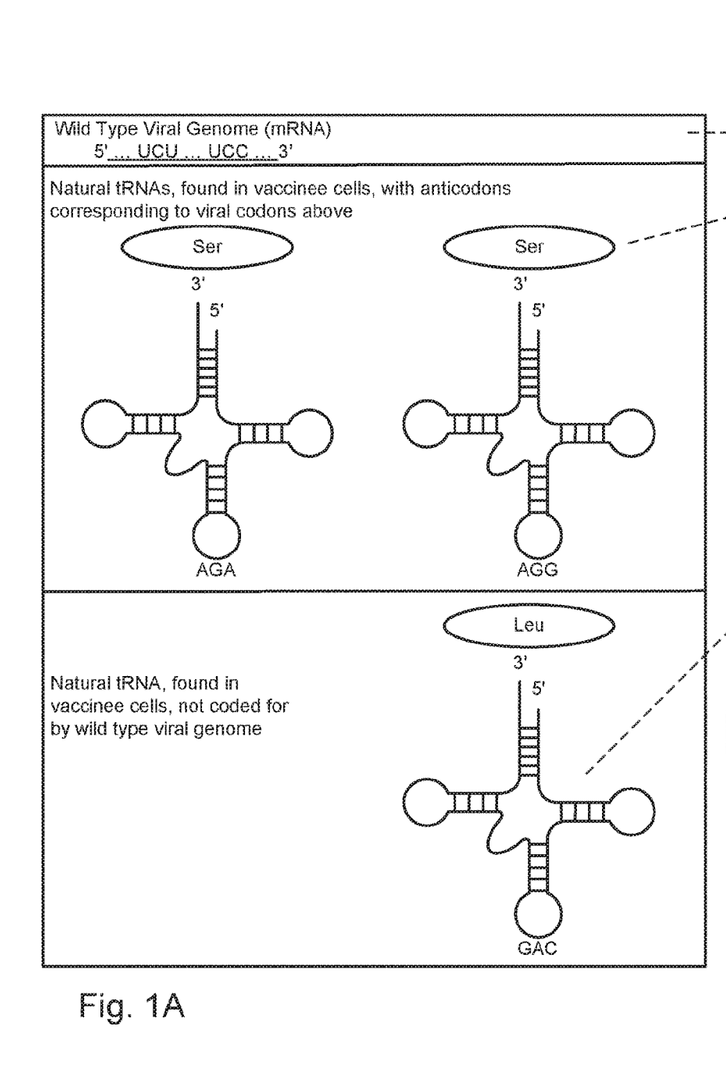
FIG. 1A illustrates an example wild type viral genome (only a portion is shown here for simplicity), as well as the natural tRNAs found in the host (and therefore the vaccinee's) cells with the corresponding anticodons and charged with their natural (and hence the viral wild type) amino acids. Also shown is a natural tRNA found in the host cells, not coded for by the wild type viral genome, but which will, in this example, be coded for by the vaccine genome in host cells that do not have the artificial and mismatched tRNA.
Figure 1B:
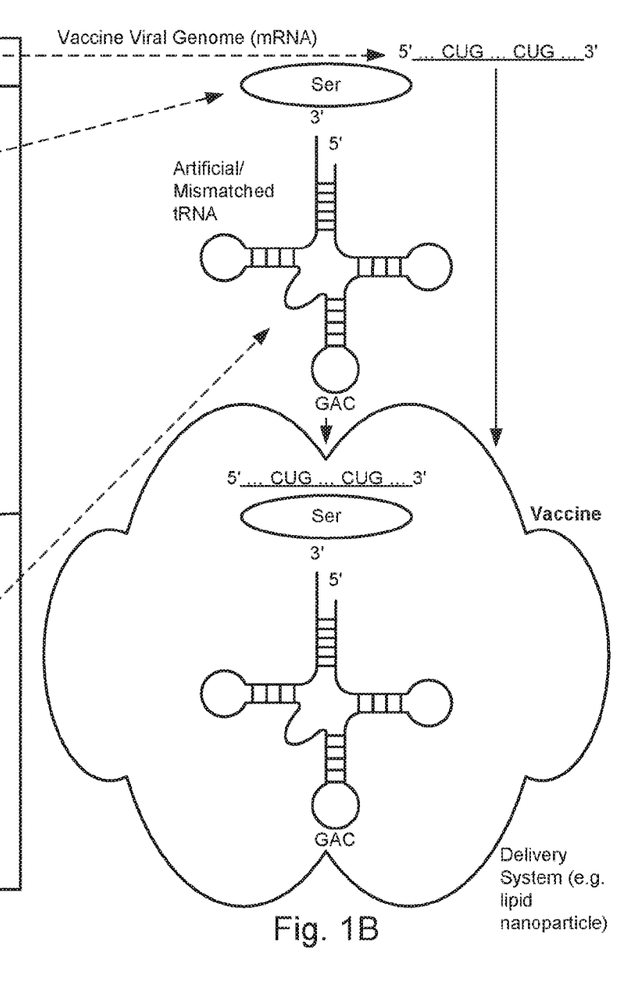
FIG. 1B illustrates the vaccine viral genome, based on the viral genome in FIG. 1A, which substitutes in this example codons naturally coding for Serine with codons that naturally code for Leucine, and the artificial and mismatched tRNA, which compensates for the vaccine viral genome substitutions with corresponding anticodons but charged with Serine. The vaccine viral genome and artificial and mismatched tRNA are combined in a single vaccine delivery system and can be considered the 'vaccine package'. (Ser=Serine; Leu=Leucine; though only a portion of the genome is shown, the entire genome would be included)
Figure 2:
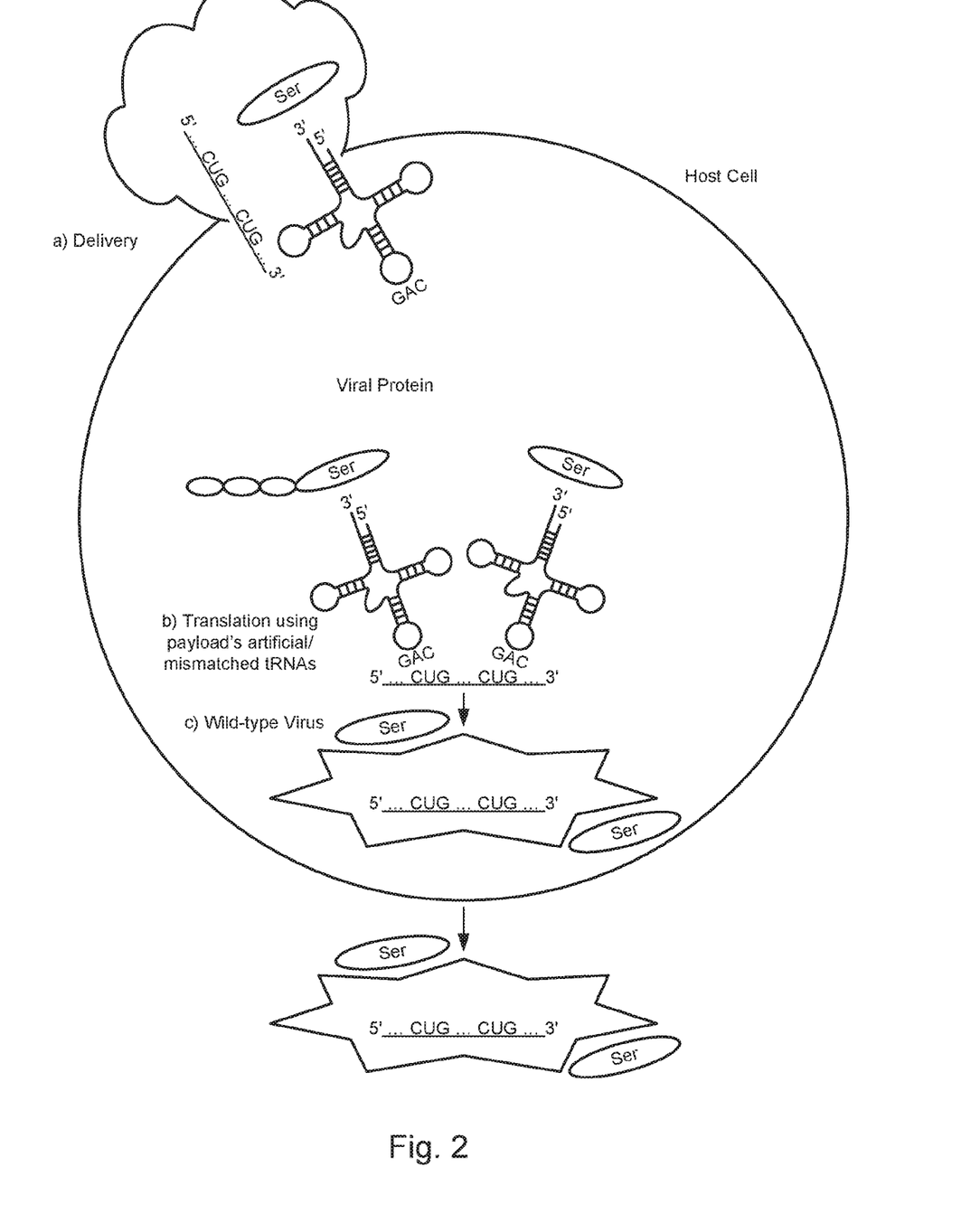
FIG. 2 illustrates the vaccine package delivered into a host cell of a vaccinee.
Figure 3:
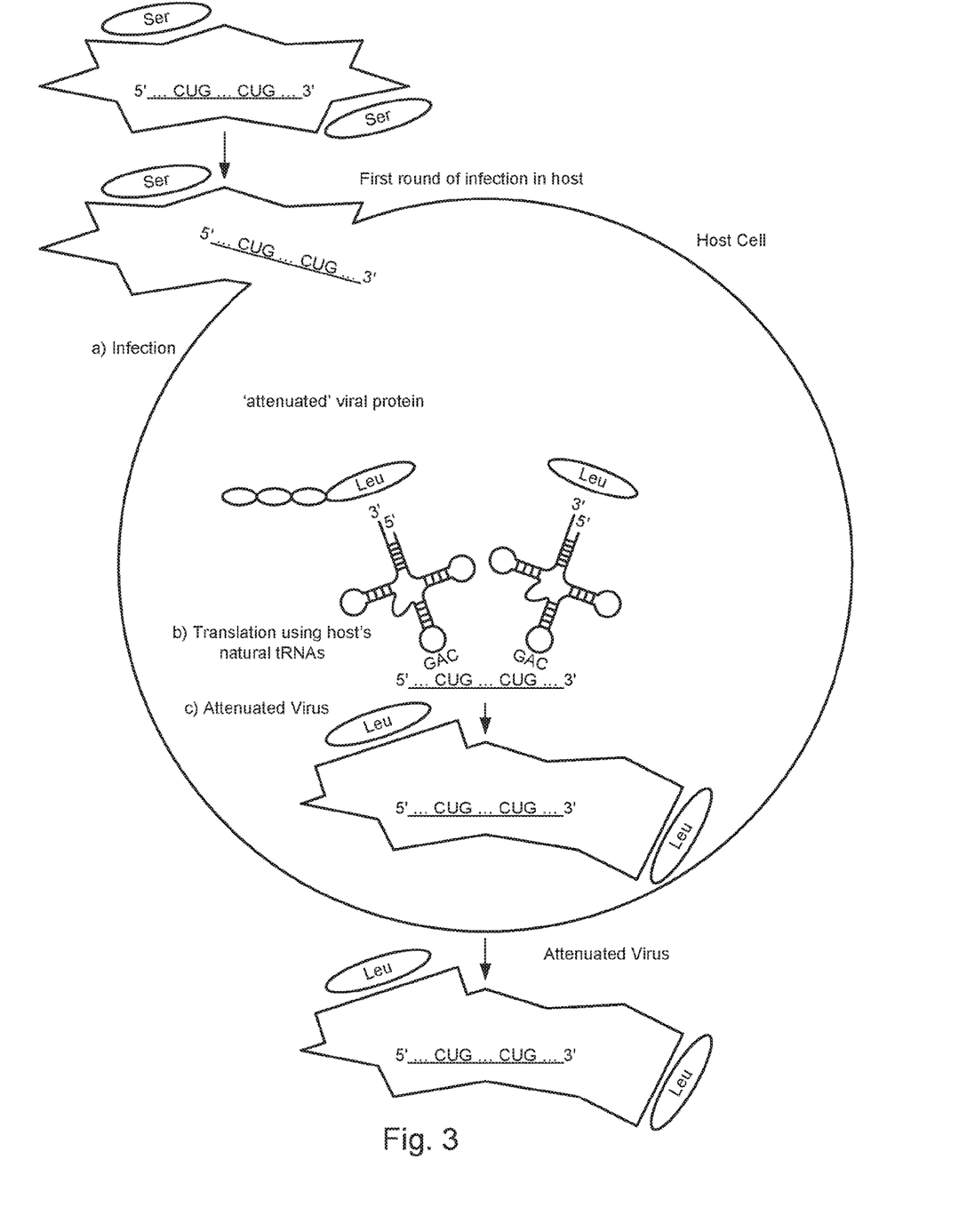
FIG. 3 illustrates the first round of infection in the host after the initial generation of phenotypically wild-type, genetically attenuated 
As used herein, "propagate" means reproduction, including but not limited to reproduction for manufacture of an attenuated virus for use in a vaccine.
Figure 4:
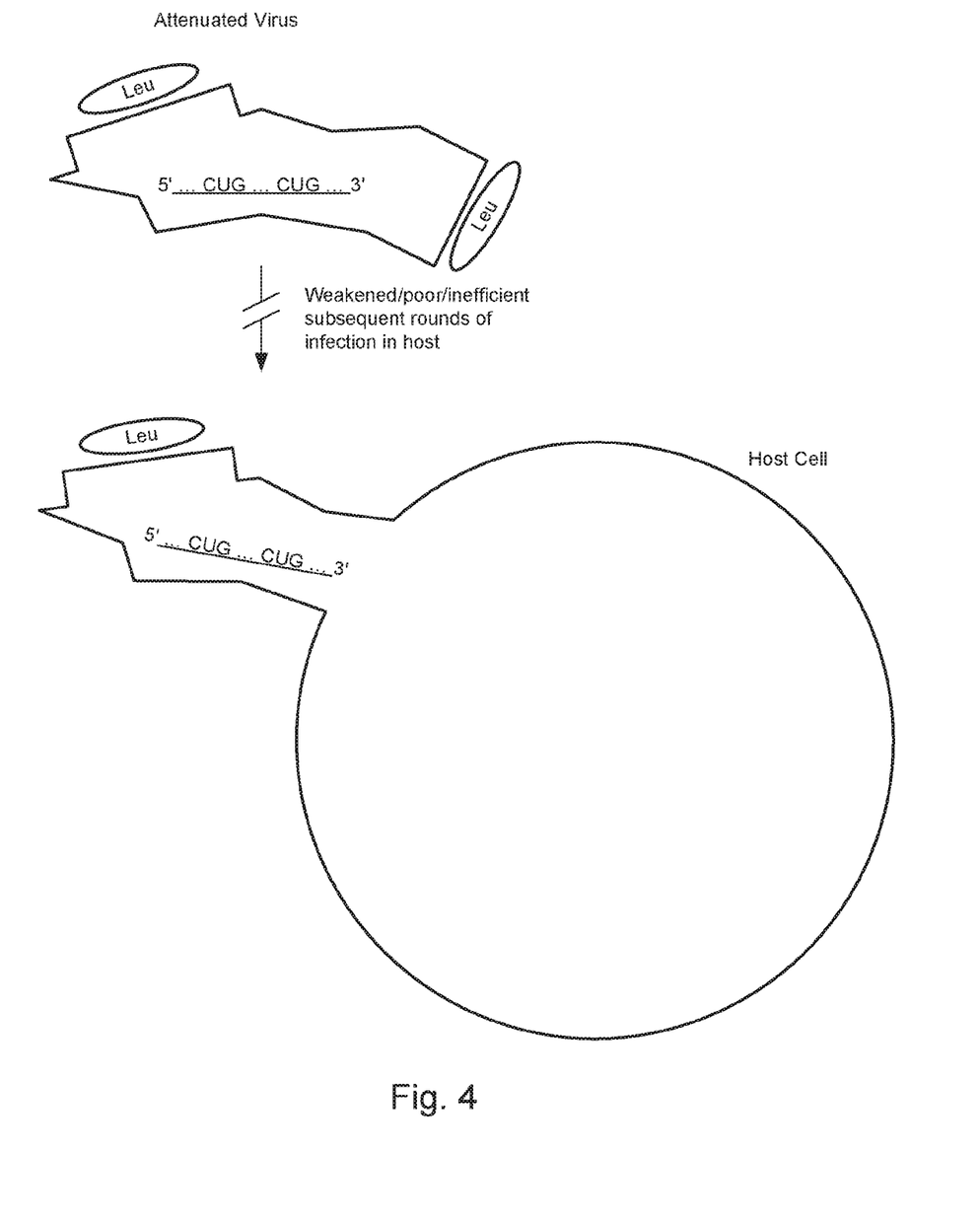

As used herein, "vaccinee" means a vaccinated subject.

Herein, examples are given which utilize the nucleotide uracil (U), used by RNA viruses. However, in the case of DNA viruses (covered by this disclosure as well), one of ordinary skill in the art would understand to substitute uracil (U) for thymine (T) to apply the disclosed methods.

The compositions and methods described herein provide genetically attenuated nucleic acid vaccines. An attenuated viral genome is introduced into the cell of a vaccinee together with unreplicable compensatory translational tools which together generate a phenotypically wild-type, genetically attenuated virus. The virus generates a relevant and robust immune response, but progeny, lacking the compensatory translational tools in their host cells, are attenuated and unable to induce disease.

It is noted that there could be instances where the codon introduced in place of the wild-type codons in the viral vaccine genome appears naturally at other locations in the genome, and translation with the artificial tRNA would result in a phenotypic mutation. In these instances, it will be necessary to replace the latter codon(s) with a different codon that codes for the wild type amino acid.

The nucleic acid vaccines described herein can be RNA vaccines or DNA vaccines or combinations of such. The nucleic acid vaccines are live attenuated whole viral genomes. Instead of vaccinating with virions, the nucleic acid encoding such a virus is introduced into the vaccinee, and the vaccinee's own cells generate the live attenuated virus. Any method of nucleic acid delivery to cells may be used with the presently disclosed methods, including but not limited to lipid nanoparticles (LNP), cationic emulsions (CNEs), electroporation, calcium phosphate/DEAE dextran methods, gene gun, or microinjection, novel methods, as well as combinations thereof.

In one embodiment, an RNA vaccine is prepared that, when translated in the vaccinee's cells which directly receive the vaccine (the "initial recipient" cells), the resultant initial round of viruses are phenotypically wild-type, but genotypically attenuated. Hence, there is approximately one round of infection by phenotypically wild-type viruses and subsequent rounds of infection are by phenotypically attenuated viruses. This can induce a robust immune response without the establishment of a disease-inducing infection.

In one aspect, to achieve this, an attenuated genome generated via the substitution of a codon encoding a first amino acid with a codon encoding a second amino acid, is delivered together with artificial 'mismatched' tRNAs that compensate for the recoding (i.e., have anticodons corresponding to the introduced codons of the second amino acid but are charged with an amino acid coded for by the codons for the first amino acid). As these mismatched tRNAs are only present in the cells initially receiving the vaccine, and not host cells infected by progeny viruses, the initial recipient cells will generate phenotypically wild-type virus encapsulating attenuated genomes, and the secondarily infected host cells, which will not have a compensatory mechanism, will consequently generate phenotypically and genetically attenuated viruses.

In one embodiment, the altered viral genome and the mismatched tRNAs are delivered in the same package. The vaccine genome should preferentially utilize the co-delivered anticodon-amino acid mismatched tRNAs over host cell's anticodon-amino acid matched tRNAs, due to physical and temporal proximity.

It is not necessary that all generated viruses are fully or even partially phenotypically wild-type. Hence, the quantity of co-delivered tRNA could be minimal.

The materials and methods described herein can be used with positive sense RNA, DNA, negative sense RNA, and double-stranded RNA viruses. Note that, when illustrating the embodiments described in this application, positive sense RNA viral genomes are described for simplicity. However, in all instances, this can be understood to be the mRNA or positive sense RNA of a negative sense RNA virus, a double stranded RNA virus, and/or a DNA virus and the described mutations would occur at the corresponding locations in the genome. Delivery of the mRNA or positive sense RNA, alone or in addition to the corresponding genome, is preferred for viruses that are not positive sense RNA viruses to allow for direct translation.

Embodiments include compositions and methods for genetically attenuated whole genome nucleic acid vaccines including, but not limited to, Picornaviruses (e.g., hepatitis A virus, enteroviruses such as poliovirus, enterovirus 71, 70, 69, and 68, Coxsackieviruses, echoviruses, foot and mouth disease virus, and rhinoviruses), Caliciviruses (e.g., hepatitis E virus, noroviruses such as Norwalk virus, feline caliciviruses), Arteriviruses (e.g., equine arteritis virus), Togaviruses (e.g., sindbis virus, the equine encephalitis viruses, chikungunya virus, rubella virus, Ross River virus, bovine diarrhea virus, hog cholera virus, Semliki forest virus), Flaviviruses (e.g., dengue virus, West Nile virus, yellow fever virus, Japanese encephalitis virus, St. Louis encephalitis virus, tick-borne encephalitis virus, bovine viral diarrhea virus, classical swine fever virus), Coronaviruses (e.g., human coronaviruses, including SARS and MERS, swine gastroenteritis virus), Rhabdoviruses (e.g., rabies virus, Australian bat lyssavirus, vesicular stomatitis viruses), Filoviruses (e.g., Marburg virus, Ebola virus), Paramyxoviruses (e.g., measles virus, canine distemper virus, mumps virus, parainfluenza viruses, respiratory syncytial virus, Newcastle disease virus, rinderpest virus, Nipah virus, Hendra virus), Orthomyxoviruses (e.g., human influenza viruses, avian influenza viruses, equine influenza viruses), Bunyaviruses (e.g., hantavirus, LaCrosse virus, Rift Valley fever virus), Arenaviruses (e.g., Lassa virus, Machupo virus), Reoviruses (e.g., human and animal reoviruses, such as rotaviruses, bluetongue virus), Birnaviruses (e.g., infectious bursal virus, fish pancreatic necrosis virus), Retroviruses (e.g., HIV 1, HIV 2, HTLV-1, HTLV-2, bovine leukemia virus, feline immunodeficiency virus, feline sarcoma virus, mouse mammary tumor virus), Hepadnaviruses (e.g., hepatitis B virus), Parvoviruses (e.g., B19 virus, canine parvovirus, feline panleukopenia virus), Papovaviruses (e.g., human papillomaviruses, SV40, bovine papillomaviruses), Adenoviruses (e.g., human, canine, bovine, and porcine adenoviruses), Herpesviruses (e.g., herpes simplex viruses, varicella-zoster virus, infectious bovine rhinotracheitis virus, cytomegalovirus, human herpesvirus 6, human herpesvirus 7, human herpesvirus 8, Epstein-Barr virus), Poxviruses (e.g., vaccinia, fowlpoxviruses, raccoon poxvirus, skunkpox virus, monkeypoxvirus, cowpox virus, buffalopox virus, musculum contagiosum virus). Newly identified and emerging families, types, species, and strains of viruses may also be used in the compositions and methods described herein. Any virus that, when select amino acid substitutions are made, can be attenuated, may be used.

Some embodiments herein relate to compositions for genetically attenuated whole genome nucleic acid vaccines in any final form, e.g., aqueous or lyophilized/freeze-dried form. Those skilled in the art will recognize that formulations that improve thermal viral stability and prevent freeze-thaw inactivation will improve products that are liquid, powdered, freeze-dried or lyophilized and prepared by methods known in the art. After reconstitution, such stabilized vaccines can be administered by a variety of routes, including, but not limited to intradermal administration, subcutaneous administration, intramuscular administration, intranasal administration, pulmonary administration or oral administration. A variety of devices are known in the art for delivery of the vaccine including, but not limited to, syringe and needle injection, bifurcated needle administration, administration by patches or pumps, needle-free jet delivery, intradermal particle delivery, or aerosol powder delivery.

Embodiments can include compositions consisting of one or more genetically attenuated whole genome nucleic acid vaccines (as described above) and a mixture of one or more excipients (e.g., high molecular weight surfactants and one or more proteins in a physiologically acceptable buffer). In certain embodiments, compositions may or may not include, but are not limited to one or more nucleic acid vaccines, one or more high molecular weight surfactants, one or more proteins, and one or more carbohydrates, in a physiologically acceptable buffer.

In another aspect, substitutions can be made for multiple different amino acids by making substitutions at, and providing compensating tRNAs for, codons in the wild type genome encoding more than one type of amino acid. The amino acids substituted in can be the same for all amino acids substituted out or different for each type of amino acid substituted out.

In another aspect, genotypic attenuation can be more extreme (by selecting the number and nature of codon substitutions), to the point where, after the generation of phenotypically wild-type viruses from the first cells, the subsequent round of replication results in the generation of viral proteins, but viable viral progeny cannot be generated. Namely, a wild-type like initial infection but no subsequent infection, only production of large amounts of wild-type viral proteins for presentation to the host immune system.

In another aspect, for a subunit-only vaccine, one can use the methods described in this invention for the generation and delivery of an attenuated nucleic acid vaccine that encodes just a portion of a viral genome, and generates wild-type viral subunits, to reduce the likelihood that the delivered nucleic acid recombines with co-infecting viruses and generates pathogenic variants in the population. The method described in this paragraph would not protect against such recombination, but would increase the likelihood that the resultant recombinant would not encode a wild-type version of the nucleic acid delivered.

Pharmaceutical Compositions

Embodiments herein provide for administration of compositions to subjects in a biologically compatible form suitable for pharmaceutical administration in vivo. By "biologically compatible form suitable for administration in vivo" it is meant a form of the active agent (e.g. live, attenuated virus composition of the embodiments) to be administered in which any toxic or otherwise adverse effects are outweighed by the therapeutic or prophylactic effects of the active agent. Administration of a therapeutically or prophylactically active amount of the therapeutic or prophylactic composition is defined as an amount effective, at dosages and for periods of time necessary to achieve a desired result, including but not limited to increased immunity to a viral pathogen. For example, a therapeutically or prophylactically active amount of a compound may vary according to factors such as the disease state, age, sex, and weight of the individual, and the ability of formulations to elicit a desired response in the individual, including but not limited to a response which boosts immunity to a viral pathogen. Dosage regimen may be adjusted to provide the optimum therapeutic and/or prophylactic response.

In some embodiments, composition (e.g. pharmaceutical chemical, protein, peptide of an embodiment) may be administered in a convenient manner such as subcutaneous, intravenous, intramuscular, intradermal, by oral administration, inhalation, transdermal application, intravaginal application, topical application, intranasal or rectal administration. In a more particular embodiment, the product may be orally or subcutaneously administered. In another embodiment, the product may be administered intravenously. In one embodiment, the product may be administered intranasally, such as inhalation. In another embodiment, the product may be administered intramuscularly. In another embodiment, the product may be administered intradermally.

Kits

Further embodiments concern kits for use with methods and compositions described herein. Compositions and nucleic acid vaccines may be provided in the kit. The kits may also comprise bioinformatics tools (e.g., for the rapid assisted genetic design of the viral vaccines described herein), and/or can include a suitable container, nucleic acid vaccine compositions detailed herein and optionally one or more additional agents such as other anti-viral agents, anti-fungal, anti-bacterial and/or anti-parasite agents.

EXAMPLES

The following examples are provided for illustrative purposes only and are not intended to limit the scope of the invention as defined by the appended claims. All examples described herein were carried out using standard techniques, which are well known and routine to those of skill in the art.

Example 1

(1) Generate a virus where codon 1 (which encodes amino acid 1, 'aa1') is substituted for codon 2 (which normally encodes aa2). Ensure there are no other natural occurrences of codon 2 in the genome.

(2) Generate tRNAs (referred to as 'mismatched tRNAs') with anticodon 2 that carry aa1.

(3) Co-deliver altered viral RNA+mismatched tRNA in a nucleic acid vaccine delivery system. (e.g., a lipid nanoparticle, cationic emulsion, or electroporation, as described in the literature.)

If the viral genome (e.g. the RNA vaccine) is translated in the presence of the mismatched tRNAs, codon 2 will be translated as aa1, producing phenotypically wild-type virus which are genotypically attenuated. However, when translated in a cell without the mismatched tRNA, such as in subsequently infected cells (cells infected with the progeny viruses from the initial cells), codon 2 will be translated as aa2, producing phenotypically and genotypically attenuated viruses.

| | Amino acid on corresponding tRNA | |
|---|---|---|
| Codon | Standard Code (Vaccinee's Code) | Artificial/mismatched tRNA |
| UCU | S | |
| UCC | S | |

| | Amino acid on corresponding tRNA | |
|---|---|---|
| Codon | Standard Code (Vaccinee's Code) | Artificial/mismatched tRNA |
| UCA | S | |
| UCG | S | |
| AGU | S | |
| AGC | S | |
| CUG | L | S |
| CUA | L | |
| CUC | L | |
| CUU | L | |
| UUG | L | |
| UUA | L | |

CUG, in the Standard Code, codes for Leucine (a neutral non-polar amino acid), as do UUA, UUG, CUU, CUC, CUA. UCU, UCC, UCA, UCG, AGU and AGC code for Serine (a neutral polar amino acid).

Wild-type animal virus (positive-sense mRNA virus) sequence: AUG (M) AUA (I) ACA (T) UCU (S) AAA (K) AGA (R) UCC (S) (SEQ ID NO: 1) . . .

(Wild-type virus is thus: M I T S K R S (SEQ ID NO: 2) . . . )

(1) Recode virus sequence as: AUG AUA ACA CUG AAA AGA CUG (SEQ ID NO: 3) . . .

(in human/animal cells, this would translate to M I T L K R L (SEQ ID NO: 4) . . . )

(2) Generate tRNAs with the anticodon of CUG (i.e., CAG) that carry Serine.

(3) Co-formulate the recoded virus sequence and the CAG-Serine tRNAs for co-delivery and vaccinate with the resultant vaccine.

In the initially infected cells, the transcript may be translated as a mixture of M I T L K R L (SEQ ID NO: 4), M I T S K R L (SEQ ID NO: 5), M I T L K R S (SEQ ID NO: 6), and M I T S K R S (SEQ ID NO: 2).

The former three will likely all be defective, at least in part, due to use of the naturally-occurring Leucine tRNAs (with the CAG anticodon).

The latter, generated with the mismatched Serine tRNAs (with the CAG anticodon), will ideally constitute the greatest fraction due to temporal and physical proximity of the viral genome to the mismatched tRNA during translation. They will be phenotypically wild-type and begin an effective round of wild-type-like infection. Yet, because they are genotypically attenuated and the subsequently infected cells will not harbor the modified tRNAs, subsequent rounds of infection will be initiated by phenotypically and genotypically attenuated viruses.

What is claimed is:

1. A method of making a nucleic acid vaccine comprising:
substituting one or more codons for a first amino acid encoded by a viral nucleic acid with a codon for a second, different amino acid resulting in a modified viral nucleic acid,
artificially charging one or more tRNAs, having an anticodon corresponding to the introduced codon coding for the second amino acid, with the first amino acid, and packaging the modified viral nucleic acid and artificially charged tRNA in a delivery system for co-delivery to a vaccinee.

2. The method of claim 1, wherein the viral nucleic acid is selected from positive sense RNA, DNA, negative sense RNA, double-stranded RNA, mRNA and combinations thereof.

3. The method of claim 1, wherein the delivery system is selected from lipid nanoparticle, cationic emulsion (CNE), medium for electroporation, and combinations thereof.

4. The method of claim 3, wherein the lipid nanoparticle is a liposome.

5. The method of claim 1, wherein the viral nucleic acid is a whole viral genome.

6. The method of claim 1, wherein the viral nucleic acid is a portion of a viral genome.

7. The method of claim 1, wherein the virus is selected from the group consisting of Influenza virus, respiratory syncytial virus (RSV), poliovirus, Hepatitis C virus, West Nile virus, Zika virus, Chikungunya virus, Ebola virus, Lassa virus, Dengue virus, SARS coronavirus, Middle East Respiratory Syndrome (MERS) coronavirus, Cytomegalovirus, Herpes Simplex viruses, Rabies virus, Foot and Mouth Disease Virus, Noroviruses, Enteroviruses, newly emerging viruses, as well as combinations thereof.

8. The method of claim 1, wherein the vaccine is a human, livestock, a bird, a household pet, wildlife, or a plant.

9. A nucleic acid vaccine produced by a method comprising:

substituting one or more codons for a first amino acid encoded by a viral nucleic acid with a codon for a second, different amino acid resulting in a modified viral nucleic acid, artificially charging one or more tRNAs, having an anticodon corresponding to the introduced codon coding for the second amino acid, with the first amino acid, and packaging the modified viral nucleic acid and artificially charged tRNA in a delivery system for co-delivery to a vaccinee.

10. The nucleic acid vaccine of claim 9, wherein the viral nucleic acid is selected from positive sense RNA, DNA, negative sense RNA, double-stranded RNA, mRNA and combinations thereof.

11. The nucleic acid vaccine of claim 9, wherein the delivery system is selected from lipid nanoparticle, cationic emulsion (CNE), medium for electroporation, and combinations thereof.

12. The nucleic acid vaccine of claim 11, wherein the lipid nanoparticle is a liposome.

13. The nucleic acid vaccine of claim 9, wherein the viral nucleic acid is a whole viral genome.

14. The nucleic acid vaccine of claim 9, wherein the viral nucleic acid is a portion of a viral genome.

15. The nucleic acid vaccine of claim 9, wherein the virus is selected from the group consisting of Influenza virus, respiratory syncytial virus (RSV), poliovirus, Hepatitis C virus, West Nile virus, Zika virus, Chikungunya virus, Ebola virus, Lassa virus, Dengue virus, SARS coronavirus, Middle East Respiratory Syndrome (MERS) coronavirus, Cytomegalovirus, Herpes Simplex viruses, Rabies virus, Foot and Mouth Disease Virus, Noroviruses, Enteroviruses, newly emerging viruses, as well as combinations thereof.

16. The nucleic acid vaccine of claim 9, wherein the vaccine is a human, livestock, a bird, a household pet, wildlife, or a plant.

* * * * *

UNITED STATES PATENT AND TRADEMARK OFFICE
CERTIFICATE OF CORRECTION

PATENT NO. : 11,154,607 B2
APPLICATION NO. : 16/616402
DATED : October 26, 2021
INVENTOR(S) : Laura Shackelton and Matthew Kerner It is certified that error appears in the above-identified patent and that said Letters Patent is hereby corrected as shown below:

In the Claims

• Claim 8 (Column 11, Line 64): please replace "vaccine" with "vaccinee"

• Claim 16 (Column 12, Line 65): please replace "vaccine" with "vaccinee"

Signed and Sealed this
Seventeenth Day of May, 2022

Katherine Kelly Vidal
*Director of the United States Patent and Trademark Office*